(12) United States Patent
Seguin et al.

(10) Patent No.: US 6,335,457 B1
(45) Date of Patent: Jan. 1, 2002

(54) COMPLEX CONTAINING BIOLOGICALLY ASSIMILABLE ORTHOSILICIC ACID, WHICH IS UNDER SOLID FORM, STABLE AND CONCENTRATED, AND A PROCESS FOR PREPARATION OF SAID COMPLEX

(75) Inventors: Marie-Christine Seguin; Jean Gueyne, both of Monaco (MC)

(73) Assignee: Exsymol S.A.M., Monaco (MC)

(*) Notice: Subject to any disclaimer, the term of this patent is extended or adjusted under 35 U.S.C. 154(b) by 0 days.

(21) Appl. No.: 09/686,882

(22) Filed: Oct. 12, 2000

(30) Foreign Application Priority Data

Oct. 15, 1999 (FR) .................................................. 99 13062

(51) Int. Cl.$^7$ ................ C07F 7/10; C07F 7/08; A61K 38/00
(52) U.S. Cl. .................. 556/413; 556/413; 556/419; 556/482; 530/300; 530/343; 530/345; 424/484; 424/70.12; 424/70.14; 424/489; 424/499
(58) Field of Search ................... 530/300, 343, 530/345; 556/400, 413, 419, 482; 514/63; 424/484, 70.12, 70.14, 489, 499

(56) References Cited

U.S. PATENT DOCUMENTS 6,001,389 A 12/1999 Seguin et al. ................ 424/434

FOREIGN PATENT DOCUMENTS

| FR | 2122529 | 9/1972 |
| JP | 9-164761 | 6/1997 |
| WO | WO 95/21124 | 8/1995 |

*Primary Examiner*—Paul F. Shaver
(74) *Attorney, Agent, or Firm*—James C. Lydon

(57) ABSTRACT

The invention concerns a complex containing biologically assimilable orthosilicic acid and a process of preparation of said complex.

In this complex, orthosilicic acid is complexed with a polypeptide and the complex is under solid, stable and concentrated form.

The present invention also concerns cosmetic or therapeutic compositions, and a nutritional supplement containing said complex.

6 Claims, No Drawings

COMPLEX CONTAINING BIOLOGICALLY ASSIMILABLE ORTHOSILICIC ACID, WHICH IS UNDER SOLID FORM, STABLE AND CONCENTRATED, AND A PROCESS FOR PREPARATION OF SAID COMPLEX

The present invention concerns a complex containing biologically assimilable orthosilicic acid, which is under solid form, stable and concentrated, and a process of preparation of said complex.

Silicon is an essential element for life. It has both a structural role being a constituent of the proteins-glycosaminoglycanes complexes found in the connective tissue's matrix, and a metabolic role on growth and osteogenesis (silicon favours the process of mineralisation of the bone). Thus, silicon is compulsory for a normal development of bones and connective tissue.

It was also shown that silicon under the form of orthosilicic acid $Si(OH)_4$ has a high affinity for $Al^{3+}$ ions and enhances their elimination. Thus, it could act against the toxic effects of aluminium on bones and brain, especially in neurologic degenerative diseases such as Alzheimer's disease.

These data suggest that a punctual supply in silicon can be very helpful, during the growing period for instance, or in particular pathologies.

Nevertheless, it is also important to prevent silicon deficiency,: several studies performed on human showed that silicon decreases with aging in skin and arteries walls, essentially because of the decrease of gastro-intestinal absorption of silicon in the course of time.

The main problem with silicon metabolism arises from the difficulty of its assimilation. Although silicon is a very abundant element, it naturally occurs under the form of minerals insoluble in water (crystalline oxides (silicas and silicates) or amorphous (clays, opals, . . . )), which do not represent a source of assimilable silicon for the organism.

Likewise, silicon as it naturally occurs in our food, i.e. essentially under the form of aluminosilicates or silica, is very slightly assimilable. The actual techniques of purification and refining of vegetable products (dietary cereals and fibres are the main source of silicon), which tend to eliminate the parts rich in silicon (the husks), have still reduced this supply.

It seems now admitted that a biologically active form of silicon must be hydrosoluble, and that the solubility depends on the amount of free OH groups (silanol functions) on the silicon atom.

In blood and extravascular liquids, the silicon is physiologically present under hydrated form of orthosilicic acid $(Si(OH)_4)$, non dissociated at the pH of the organism, and almost completely in its free form.

Moreover, studies have shown that only monomeric or oligomeric (very slightly polimerized) orthosilicic acid is able to pass the intestinal barrier (P. Creach, J. Adrian, Méd. et Nut. 1990, 26(2), 73–90).

The presence on the silicon atom of free OH groups is closely linked to its biological role. Indeed, these functions can make covalent or hydrogen bonds with amides, water, alcohols, ketones, esters, . . . .

Thus, in biological media, bonds with the membrane's phospholipids, proteins, glycosaminoglycanes and polysaccharides can be formed.

So it is necessary to conceive a silicon supply in which silicon is under the form of silicic acid or a form as similar as possible.

Monomeric orthosilicic acid in solution is relatively stable until a concentration of about $10^{-4}$ $Mol.l^{-1}$; but, when the concentration increases, the $Si(OH)_4$ molecules associate to make oligomers and polymers of orthosilicic acid (formation of siloxane bonds Si—O—Si) to finally make colloidal solutions or silica gels that are weakly soluble or insoluble in water, and which silicon biodisponibility is very weak.

The supply of orthosilicic acid under the form of very diluted stable solutions do not comply with a daily supplementation in silicon and also make impossible its incorporation, in sufficiently high amounts, in nutrients or dietetic, cosmetic or therapeutic compositions.

The already available sources of biologically active and concentrated silicon are organosilicic compounds presenting several free hydroxyl groups, that can be found under the form of solutions or under solid form (EP- 0 289 366 and FR 2 761 074 patents).

Besides, more concentrated solutions of orthosilicic acid are available, in which orthosilicic acid is stabilized by a very acid pH that counteracts the polymerization by hydrolyzing the siloxane bonds Si—O—Si (patent JP 58176115).

The patent WO 95/21124 also proposes concentrated preparations of orthosilicic acid stabilized by a stabilizer. A complex between orthosilicic acid and choline in solution is made, but a good stability can not be obtained without maintaining an acid pH.

Such acid solutions do not provide an optimal assimilation because during ingestion, the pH conditions are not maintained (physiological pH). An important part of the orthosilicic acid polymerizes before being assimilated.

In the scope of a medical study, a topical application of colloidal silicic acid was combined with an oral intake in order to improve aged skin, fragile hair and brittle nails (Lassus A., Journal of International Medical Research 1993, 21, 209–215). However, the biodisponibility of this form is weak because of the presence of many siloxane bonds.

This is why a purpose of the invention is proposing a form of orthosilicic acid which is assimilable, concentrated and stable.

Moreover, to be orally assimilable, orthosilicic acid has to be soluble and chemically stable at the different physiological pH that is to say in acidic, neutral or slightly alkaline medium Thus an other aim of the invention is obtaining a form of orthosilicic acid which is stable at these different pH.

Lastly, an other purpose was to obtain a solid form which can be incorporated in dietetic, cosmetic or therapeutic compositions, and in nutritional supplements, under non aqueous forms: capsules, granules or tablets for oral administration.

These objectives can be reached by complexing orthosilicic acid with a polypeptide which acts as a stabilizer by forming hydrogen bonds with orthosilicic acid. This prevents the formation of siloxane bonds and orthosilicic acid polymerisation.

A stable solid form (powder) of orthosilicic acid is thus obtained which is, after ingestion, solubilized in biological fluids to release a soluble form of assimilable and biologically active orthosilicic acid (monomeric or oligomeric).

Notwithstanding the excellent stability of the concentrated solid form, an important characteristic of the invention is its ability to remain stable during its transit in the gastrointestinal tractus, and this despite the existence of different physiological pH favouring its polymerisation.

This can be explained by the particularly strong interaction existing between the silicon and the polypeptide. When dissolving, the complex between the polypeptidic chain and the hydroxylic functions carried by the silicon atom remains;

the cohesion of the complex is linked to the formation of a group of weak bonds (hydrogen bonds) and probably to the structural organisation of the polypeptidic chain.

It is to be noted that in the prospect of preparing a sustained-release form, some peptides having a pharmacological activity have been associated to natural minerals containing silicon or to synthetic minerals made of silicic acid (patent No. BE 778.239). The common characteristic of all these silicon compounds is the formation of a colloidal suspension suitable as a support for the peptides; it is clear that the technical problem treated in this patent has no connection with the present invention.

The subject of the present invention is proposing a complex containing biologically assimilable orthosilicic acid in which orthosilicic acid is complexed with a polypeptide and is under solid, stable and concentrated form.

The subject of the present invention is also to provide a process of preparation of the said complex containing orthosilicic acid, comprising the following steps:

the polypeptide is dissolved in 1 volume of distilled water the pH is adjusted between 2 and 4 in a proportion comprised between 1/4 and 1 volume, an alcohol soluble in water, preferably ethanol, is added under stirring, a hydrolyzable precursor of orthosilicic acid, preferably a tetraalkoxysilane, is added dropwise the mixture is maintained under stirring until complete hydrolysis of the precursor alcohol and water are evaporated.

An orthosilicic acid-polypeptide complex is thus obtained, which is under the form of a powdery, slightly colored solid, having a silicon content up to 10%. Preferably, the silicon content is comprised between 1 and 5%.

Following an advantageous embodiment of the invention, the polypeptide is a hydrolysate of proteins from animal or vegetable origin.

In fact, it was established that polypeptides obtained after strong hydrolysis were the most appropriate for the realisation of the purposes of the invention.

The polypeptides of high molecular weight, and particularly certain proteins, appeared to be bad stabilizers. This may be explained by the tertiary structure of these proteins which is not suitable with a stabilizing arrangement with orthosilicic acid.

Following a preferred embodiment of the invention, the polypeptide is a collagen hydrolysate, such as porc or fish collagen.

In fact, among proteins hydrolysates from animal origin, the collagen hydrolysate is particularly suitable since collagen has a structure that favours the formation of a complex with orthosilicic acid.

Besides, silicon is strongly associated to collagen in vivo (Carlisle EM, The Science of Total Environment, 1988, vol.73, 95–106).

Lastly, an other aim of the present invention is to propose cosmetic or therapeutic compositions and also a nutritional supplement containing, in association with any suitable excipient, such a complex.

Among the numerous uses of these nutritional compositions and supplements can be mentioned: silicon deficiencies, need of an important intake for pregnant woman, growing child, or elderly people for whom both silicon assimilation ability and tissular binding are reduced, for regeneration and strengthening of skin, hair, nails or prevention and treatment of diseases such as osteoporosis or atherosclerosis.

The following examples intend to illustrate in a non restrictive way the present invention.

EXAMPLE 1

Preparation of an Orthosilicic Acid Powder at 1,5% in Silicon With a Hydrolyzed Nutritious Gelatine of Porcine Origin 90 g of porcine proteins hydrolysate are dissolved under stirring in 250 ml of distilled water. The pH is adjusted between 3 and 4 with a 6 N hydrochloric acid solution.

270 ml of absolute ethanol are then slowly added under stirring. An homogenous orange-yellow solution is obtained, which is very slightly opalescent.

Next, tetraethoxysilane (11.25 g) is added dropwise to the mixture, under stirring.

The solution is maintained under stirring until complete hydrolysis of the precursor.

Alcohol and water are evaporated under reduced pressure. 92 g of a powdery, slightly colored (yellowish) solid are obtained, which residual content of water is about 5.5%.

EXAMPLE 2

Preparation of a Powder of Orthosilicic Acid With a Wheat's Proteins Hydrolysate 180 g of wheat's proteins hydrolysate are dissolved under stirring in 500 g of distillated water. 400 ml of absolute ethanol are added. The mixture is acidified with a diluted hydrochloric acid solution.

23 g of tetraethoxysilane are then added dropwise to the mixture, under stirring.

Next, ethanol and water are eliminated by distillation under reduced pressure.

A slightly colored solid is obtained, which can be crushed to obtain a powder perfectly soluble in water with a silicon content of about 2.5%.

EXAMPLE 3

Stability Study

This study was carried out at 37° C. (±3° C.) with aqueous solutions having a silicon content of 0.075%, at stomachal pH (1.2) and intestinal pH (7.5). The stability criterion is the solubility of the silicon.

|  | pH 1.2 | pH 7.5 |
|---|---|---|
| Soluble Si content at t0 (g/Kg) | 0.75 | 0.75 |
| Soluble Si content at t + 8 h (g/Kg) | 0.75 | 0.6 |
| Soluble Si content at t + 24 h (g/Kg) | 0.7 | 0.45 |

EXAMPLE 4

Diffusion Tests on Duodenum

The assimilation, at the duodenal wall level, of different forms of silicon in aqueous solution (0.6 in % Si) is measured and compared. The different forms tested are the following: a solution obtained by dissolution of a powder of orthosilicic acid stabilised by a collagen polypeptide, a solution containing non stabilised orthosilicic acid and a sodium silicate solution.

Sprague Dawley rats are sacrificed by intracardiac injection of disodium pentobarbital. Immediately after sacrifice, the duodenum of each rat is recollected, and washed with a NaCl (0.9%) solution. After introduction of about exactly 1 ml of the silicon solutions, the organs are ligatured with cotton thread and placed in 10 ml of a buffered isotonic solution at 37° C. At different times of the study, 1 ml of the buffered isotonic solution is sampled and filtered. The concentration of soluble silicon is measured by the atomic absorption technique.

The silicon solutions for duodenum are adjusted to duodenal particular pH (8.5).
Results:

| Complexed Orthosilicic acid | | Sodium silicate | | Non stabilised orthosilicic acid | |
|---|---|---|---|---|---|
| Time (min) | % of silicon diffusion | Time (min) | % of silicon diffusion | Time (min) | % of silicon diffusion |
| 0 | 0 | 0 | 0 | 0 | 0 |
| 23 | 1.55 | 24 | 0.83 | 24 | 0.67 |
| 31 | 2.07 | 28 | 0.91 | 28 | 0.99 |
| 39 | 2.59 | | | 34 | 1 |
| 53 | 3.5 | 52 | 1.38 | 48 | 1.16 |
| 57 | 3.76 | 56 | 1.47 | 56 | 1.54 |
| | | 60 | 1.55 | 60 | 1.75 |
| 65 | 4.28 | 66 | 1.67 | 68 | 1.86 |
| 73 | 5.8 | 70 | 1.75 | 70 | 2.08 |
| 74 | 4.87 | 74 | 1.83 | 74 | 2.13 |
| 82 | 5.39 | 86 | 2.07 | 85 | 2.54 |
| 90 | 6.2 | 90 | 2.15 | 90 | 2.67 |

These results show that the orthosilicic acid complexed with a polypeptide diffused twice more than non stabilised orthosilicic acid and three more times than sodium silicate (these later forms have a weak diffusion).

Only the complexed form diffused and so was assimilated. This confirms that biologically active orthosilicic acid have to be soluble in water and stable at tissular pH.

EXAMPLE 5

Nutritional Supplement for Improving Phaners, Hair and Nails Growth, Under the Form of a Powder for Drinkable solution

| | | |
|---|---|---|
| Vegetable proteins | | 90 g |
| Vitamin E | | 100 mg |
| Iron | | 60 mg |
| Zinc | | 14 mg |
| Magnesium | | 450 mg |
| Silicon under the form of complexed orthosilicic acid powder at 1.5% in Si | | 70 mg |
| Excipients (sodium bicarbonate, saccharose) | qsp | 100 g |

This supplement is under the form of a powder for drinkable solution in sachets of 7 g. The posology is 1 sachet/day which correspond to a silicon intake of 5 mg under the form of a powdery orthosilicic acid complex at 1,5% in silicon (corresponding to 0,33 g of complex).

EXAMPLE 6

Therapeutic Composition for: Osteoporosis, Arthrosis, Arteriosclerosis of the Lower Limbs

| | | |
|---|---|---|
| Silicon under the form of complexed orthosilicic acid powder at 1.5% in Si | | 750 mg |
| Lactose | qsp | 100 g |

This composition is under the form of tablets of 0.33 g each, corresponding to 2.47 mg of silicon under the form of orthosilicic complex at 1.5% (equivalent to 0.165 g of complex). The recommended daily intake is 2 tablets.

What is claimed is:

1. Complex containing biologically assimilable orthosilicic acid, wherein orthosilicic acid is complexed with a polypeptide and under solid, stable and concentrated form.

2. Complex according to claim 1, wherein said polypeptide is a protein hydrolysate of animal or vegetable origin.

3. Complex according to claim 1, wherein said polypeptide is a collagen hydrolysate, such as pork or fish collagens.

4. Process of preparation of a complex according to claim 1, comprising the following steps:

the polypeptide is dissolved in 1 volume of distillated water the pH is adjusted between 2 et 4 in a proportion comprised between 1/4 and 1 volume, an alcohol soluble in water (preferably ethanol) is added under stirring a hydrolysable precursor of orthosilicic acid, preferably tetraalkoxysilane, is introduced dropwise the mixture is maintained under stirring until complete hydrolysis of the precursor alcohol and water are evaporated.

5. Cosmetic or therapeutic composition comprising, in association with any suitable excipient, a complex containing biologically assimilable orthosilicic acid according to claim 1.

6. Nutritional supplement comprising, in association with any alimentary suitable excipient, a complex containing biologically assimilable orthosilicic acid according to claim 1.

* * * * *